United States Patent [19]

Yang et al.

[11] Patent Number: 4,490,561

[45] Date of Patent: Dec. 25, 1984

[54] METHOD FOR ALKOXYLATING FLUORINATED ALCOHOLS

[75] Inventors: Kang Yang; Charles M. Starks; O. Carl Kerfoot, all of Ponca City, Okla.

[73] Assignee: Conoco Inc., Ponca City, Okla.

[21] Appl. No.: 541,811

[22] Filed: Oct. 13, 1983

[51] Int. Cl.³ ............................................. C07C 41/03
[52] U.S. Cl. ................................... 568/615; 568/606; 564/96; 564/209
[58] Field of Search ................. 568/615, 606; 564/96, 564/209

[56] References Cited

FOREIGN PATENT DOCUMENTS 570590 9/1977 U.S.S.R. ............................. 568/615

Primary Examiner—Howard T. Mars
Attorney, Agent, or Firm—Cortlan R. Schupbach

[57] ABSTRACT

Fluorinated alcohols are alkyoxylated using catalysts which provide reaction products having low surface tensions and which are stable in severe acidic conditions.

6 Claims, No Drawings

METHOD FOR ALKOXYLATING FLUORINATED ALCOHOLS

This invention relates to the production of alkoxylated fluorinated alcohols by reacting such alcohols with an alkoxylating agent in the presence of certain catalysts. More particularly, this invention relates to the production of alkoxylated fluorinated alcohols by reacting such alcohols with alkoxylating agents to yield a fluorinated alcohol product having a peaked alkoxylating unit distribution, very low surface tension, and which is stable in highly reactive substances such as strong acids or bases. These alkoxylated alcohols contain low amounts of by-products and contaminants.

Fluorinated alcohols are starting materials for a group of fluoro-surfactants which possess surfactant and chemical properties differing widely from non-fluorinated surfactants. Such fluorosurfactants are highly surface active materials which are more effective than totally hydrocarbon surfactants in wetting, dispersing and emulsifying properties or for use in systems wherein hydrocarbon based surfactants are destroyed, such as in strong acid or base systems. Generally, these powerful surface active agents are effective at very low concentrations.

Such fluorinated alcohol alkoxylates (or fluorosurfactants) are normally prepared using acid or base system much as is done with hydrocarbon base surfactants. For example, when fluorinated alcohols which are alkoxylated by the use of an acid catalyst such as $BF_3$, formation of side products such as dioxane, polyethylene glycol and the like becomes excessive, requiring removal of these materials before end use of the fluorosurfactant. In addition, use of many base catalysts have been found ineffective for alkoxylation of some fluorinated alcohols, since methods of preparing these alcohols produces contaminants which makes such base catalysts inactive and thus ineffective. The combination of high by-products and low reactivity of catalysts make such alkoxylated fluorinated alcohols extremely expensive surfactants, suitable only for specialty uses where hydrocarbon surfactants are decomposed or are ineffective.

Fluorinated alcohols themselves are well known in the art. Representative but non-exhaustive examples of such art are French Pat. No. 1,438,617, U.S. Pat. Nos. 2,666,797; 2,803,656; 3,102,103; 3,171,861; 3,283,012; and 3,285,975. These patents generally describe the different types of fluorinated alcohol which form the basis for fluorinated surfactants and which are useful in the practice of the present invention. Therefore, these patents are incorporated by reference into the instant specification.

It would be of great benefit to provide an improved process for alkoxylating such fluorinated alcohols in order to obtain fluorosurfactants, while providing a product with less by-products and contaminants and at a higher rate than provided by current processes.

We have now discovered that such fluorinated alcohols can be alkoxylated rapidly and with low amounts of by-products when using a process which comprises contacting said fluorinated alcohols with an alkoxylating agent in the presence of a catalyst, at temperatures of from about 90° C. to about 260° C., wherein the improvement comprises using as a catalyst at least one material having the general formula selected from the group consisting of (1) $(R)_{q-v}MX_x$
(2) $HF/M(OC_nR^1{}_{2n+1})_q$
(3) $BF_3/M(R)_q$ and
(4) $SiF_4/M(R)_q$ wherein M is a metal selected from the group consisting of gallium, indium, thallium, zirconium, hafnium, aluminum and titanium, v is from 1 to q−1, n is from 1 to 22, q is equal to the valence of M, and R is, independently, hydrogen, fluorine, alkyl groups containing from 1 to 20 carbon atoms, and alkoxide groups containing from 1 to 20 carbon atoms, $R^1$ is independently, hydrogen or fluorine, and X is halogen. The mole ratio of HF, $BF_3$, and $SiF_4$ to M can vary widely. Normally these mole ratios will range from about 0.1 to about 5.0, but from about 0.5 to 4.0 is preferred. The most preferred catalysts have the general formula $HF/Al(OC_nR^1{}_{2n+1})_3$ and $HF/Ti(OC_nR^1{}_{2n+1})_4$ where n is from 1 to 20.

Catalysts can be prepared in-situ when practicing the present invention. For example, aluminum alkyls can be reacted with fluoro-alcohols, producing in-situ aluminum alkoxides of fluorinated alcohols, which can be then combined with HF to produce effective HF/Al(OR$_f$)$_3$ catalysts. These reactions occur readily at ambient conditions and provide a convenient method for preportion of catalysts of the present invention.

Catalysts of the type described have been taught to be useful for alkoxylation reactions in U.S. Patent applications Ser. No. 383,387, filed June 1, 1982; U.S. Pat. No. 422,324, filed Sept. 23, 1982; and U.S. Pat. No. 414,216, filed Sept. 2, 1982. However, it is surprisingly found that these catalysts, which are taught to be useful for non-fluorinated alcohols, are likewise useful for fluorinated alcohols, and in fact are useful for these alcohols even when art catalysts useful for non-fluorinated alcohols react very slowly or are ineffective. In addition, the fluorosurfactants obtained from the process of the present invention tend to exhibit extremely low surface tension when compared to state of the art fluorosurfactants, thus providing extremely high wettability and surfactant ability not found in known fluorosurfactants.

The fluorinated alcohols which can be alkoxylated in the process of the present invention are those having at least one general formula selected from the group consisting of

(5) $R_f(CH_2)_aOH$,

(6) $R_fSO_2N-R^1OH$, with $R^2$ on N

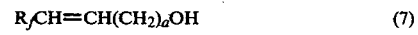

(7) $R_fCH=CH(CH_2)_aOH$

(8) $R_fCONR^1OH$, with $R^2$ on N wherein $R^1$ is alkylene groups containing from 2 to 30 carbon atoms, $R^2$ is, independently, hydrogen, halogen, or alkyl groups containing from 1 to 30 carbon atoms, a is from 1 to 12, and $R_f$ is, independently, (a) $C_mF_{2m+1}$
(b) $(CF_3)_2CF(CF_2)_m$, where m is 3 or more. Most preferred alcohols have the formula $C_mF_{2m+1}$.

Representative but non-exhaustive examples of alcohols useful in the present invention are 1,1-dihydroheptafluorobutylalcohol, trifluoroethanol, 1,1-dihydro-n-undecafluorohexanol; 1,1-dihydro-n-nonadecafluorodecanol; 1,1-dihydroperfluorodecanol; 1,1-dihydrononafluoroamyl alcohols; 1,1-dihydroundecafluorohexanol, 1,1-dihydropentadecafluorooctanol, 1,1-dihydrononadecafluorodecanol; 2-(perfluoropropy) ethanol-1. (perfluoroheptyl) ethanol-1; (perfluorodecyl) ethanol-1; 3-(perfluorobutyl)propanol-1; 3-(perfluorooctyl)propanol-1; 3-(perfluorododecyl)propanol-1; 4-(perfluorooctyl)butanol-1; 5-(perfluoropropyl)pentanol-1; (perfluorobutyl)pentanol-1; (perfluorooctyl)pentanol-1; (perfluorododecyl)pentanol-1; 6-(perfluorodecyl)hexanol-1; 7-(perfluorooctyl)heptanol-1; 8-(perfluorobutyl)octanol-1; 8-(perfluorooctyl)octanol-1; 8-(perfluorododecyl)octanol-1; 11-(perfluorobutyl)undecanol-1; 11-(perfluorooctyl)undecanol-1; 11-(perfluorododecyl)undecanol-1; 11-(perfluorododecyl)undecanol-1; 11-(perfluoro-4-ethylcyclohexyl)-undecanol-1; 12-(perfluorobutyl)-dodecanol-1; 12-(perfluorooctyl)dodecanol-1; 12-(perfluorododecyl)-dodecanol-1; N-propyl,N-ethanol(perfluorooctanesulfonamide); N-ethyl,N-hexanol(perfluorooctanesulfonamide); 1,1-dihydro(perfluorobutyl) alcohol; N-ethyl, N-undecanol(perfluorooctanesulfonamide); N-propyl,N-ethanol (perfluorooctanesulfonamide); N-butyl,N-ethanol (perfluorooctanesulfonamide); 3-(perfluorobutyl)propen-2-ol-1; 3-(perfluorooctyl)propen-2-ol-1; 3-(perfluorododecyl)propen-2-ol-1; 4-(perfluorooctyl)buten-3-ol-1; 5-(perfluoropropyl) penten-4-ol-1; 5-(perfluorobutyl)penten-4-ol-1; 5-(perfluorooctyl)penten-4-ol-1; 5-(perfluorododecyl)penten-4-ol-1; 6-(perfluorodecyl)hexen-5-ol-1; 7-(perfluorooctyl)hepten-6-ol-1; 8-(perfluorobutyl)octen-7-ol-1; 8-(perfluorooctyl)octen-7-ol-1; 8-(perfluorododecyl)octen-7-ol-1; 11-(perfluorobutyl)undecen-10-ol-1; 11-(perfluorooctyl)-undecen-10-ol-1; 11-(perfluorododecyl)undecen-10-ol-1; 11-(perfluoro-4-ethylcyclohexyl)undecen-10-ol-1; 12-(perfluorobutyl)dodecen-11-ol-1; 12-(perfluorooctyl)dodecen-11-ol-1; 12-(perfluorododecyl)-dodecen-11-ol-1.

Representative but non-exhaustive examples of catalysts having the formula

are dialkyl aluminum fluorides, alkyl aluminum difluorides, trialkyl zirconium fluorides, dialkyl zirconium difluorides, alkyl zirconium trifluorides, trialkyl titanium fluorides, dialkoxyaluminum fluorides, alkoxyaluminum difluoride, trialkoxy zirconium fluorides, dialkoxy zirconium difluorides, alkoxy zirconium trifluorides, trialkoxy titanium fluorides, dialkoxy titanium difluoride, alkoxy titanium trifluorides, dialkoxy gallium fluorides, dialkoxy indium fluoride, dialkoxy thallium fluorides, and trialkoxy hafnium fluorides. These alkyl and alkoxy groups will normally contain from about 1 to about 20 carbon atoms, but preferred catalysts are those containing from about 1 to about 14 carbon atoms.

Representative but non-exhaustive examples of catalysts having the general formula $BF_3/M(R_q)$ and $SiF4/M(R_q)$ are $BF_3$/aluminum hydride, $BF_3$/trimethylaluminum, $BF_3$/triethylaluminum, $BF_3$/tripropylaluminum, $SiF_4$/aluminum hydride, $SiF_4$ trimethylaluminum, $SiF_4$/triethylaluminum, $BF_3$/dimethyl ethyl aluminum, $SiF_4$/dimethyl ethyl aluminum, $BF_3/(C_{20}H_{41})_3Al$, $SiF_4/(C_{20}H_{41})_3Al$, $BF_3$/titanium hydride, $BF_3$/tetramethyltitanium, $BF_3$/tetraethyltitanium, $BF_3$/tetrapropyltitanium, $SiF_4$/titanium hydride, $SiF_4$/tetramethyltitanium, $SiF_4$/tetraethyltitanium, $BF_3$/dimethyl diethyl titanium, $SiF_4$/dimethyl diethyl titanium, $BF_3/(C_{20}H_{41})_4Ti$, $SiF_4/(C_{20}H_{41})_4Ti$, $BF_3$/trimethyl gallium, $BF_3$/trimethyl indium, $BF_3$/trimethyl thallium, $BF_3$/tetramethyl zirconium, $SiF_4$/tetramethyl hafnium. Mixtures of these catalysts can be used.

Catalysts which provide similar adduct distributions but which are less expensive comprise $BF_3$ and metal alkoxides, $SiF_4$ and metal alkoxides, or mixtures of these catalysts, wherein the metal alkoxides have the general formula $M(OR)_n$ where each R is, independently, hydrogen and alkyl groups containing from 1 to 20 carbon atoms each, M is aluminum or titanium, and n is 3 or 4 depending on valence of M. Preferred catalysts are those containing from 1 to 14 carbon atoms in each alkyl group.

Representative but non-exhaustive examples of such catalysts are $BF_3/(C_2H_5O)_3Al$; $BF_3/(CH_3O)_3Al$; $SiF_4/(C_2H_5O)_3Al$; $SiF_4/(CH_3O)_3Al$; $BF_3/(CH_3O)_2(C_2H_5O)Al$; $SiF_4/(CH_3O)_2(C_2H_5O)Al$; $SiF_4/(CH_3O)(C_2H_5O)_2Al$; $BF_3/(CH_3O)_3Al$; $BF_3/(C_2H_5O)_4Al$; $BF_3/(C_{20}H_{41}O)_3Al$; $BF_3/(C_2H_5O)_4Ti$; $BF_3/(CH_3O)_4Ti$; $SiF_4/(C_2H_5O)_4Ti$; $SiF_4/(CH_3O)_4Ti$; $BF_3/(CH_3O)_2(C_2H_5O)_2Ti$; $BF_3/(CH_3O)_2(C_2H_5O)_2Ti$ and $SiF_4/(CH_3O)_2(C_2H_5O)_2Ti$.

Representative but non-exhaustive examples of catalysts having the general formula $HF/M(OC_nH2_{n+1})_q$ are $HF/(CH_3O)_3Al$, $HF/(C_2H_5O)_3Al$, $HF/(CH_3O)_2(C_2H_5O)Al$, $HF/(iC_3H_7O)_3Al$, $HF/(C_{20}H_{41}O)_3Al$, $HF/(CH_3O)_4Ti$, $HF/(C_2H_5O)_4Ti$, $HF/(iC_3H_7O)_4Ti$, $HF/(CH_3O)_4Zr$, $HF/(C_2H_5O)_4Zr$, $HF/(CH_3O)(C_2H_5O)(iC_3H_7O)Al$, and $HF/(CH_3O)_2(C_2H_5O)(iC_3H_7O)Ti$.

The present invention can be carried out at temperatures of from about 20° C. to about 260° C. However, more normal temperatures range from about 90° C. to about 200° C. For most practical purposes, commercial operations will be carried out in a temperature range of about 100° C. to about 200° C.

The present invention can be carried out at ambient pressure. However, pressures above or below ambient can be used as desired. It is essential only that sufficient pressure be used to maintain alcohols present in liquid phase while undergoing alkoxylation. Normally, pressures up to about 100 pounds per square inch gauge (psig) can be used, but pressures below about 60 pounds per square inch gauge are preferred. It is simply more convenient to carry out reactions in the pressure range of from about atmospheric to about 100 psig.

The alkoxylations of the present invention are normally carried out with materials or mixtures of materials comprising alpha and beta alkylene oxides. Of these materials, ethylene oxide, propylene oxide and mixtures of these are preferred.

The fluorinated reaction products can have any desired content of adducting material. For example, in alcohol alkoxylations ethylene oxide will normally comprise from about 10 to 90% of product content based on weight. However, for many purposes the content of ethylene oxide or other adducting material will range from about 20% to about 70% by weight. The weight of adducting material present in the reaction is not critical other than the minimum amount necessary to provide sufficient units to reach the mole adduct level desired for the materials to be reacted.

For practical purposes, normally from about 0.05 to about 10 weight percent catalysts based upon the weight of the materials to be reacted is present in the reaction. These catalysts are effective in the absence of promoters or a co-catalyst although such materials can be used. Preferred levels of catalysts in the reaction mixture are from about 0.1 to about 10.0 weight percent based on the total reaction mixture weight and most preferred catalyst levels are from about 0.15 to about 5.0% by weight based on the total reaction mixture weight.

Catalysts of the present invention are normally added to the reaction mixture in a solution form, or are formed in situ. However, to render these catalysts less air sensitive and more stable, catalysts can optionally be supported on materials having active surface hydroxyl groups. Representative but non-exhaustive examples of such support materials are alumina, diatomaceous earth, silica, bentonite, glass, various clays and the like.

The instant invention is more concretely described with reference to the examples below wherein all parts and percentages are by weight unless otherwise specified. The examples are provided to illustrate the present invention and not to limit it.

Two types of fluoroalcohols, one with molecular weight 455, and the other with 490, were used in the examples presented. These alcohols have the general formula, $CF(CF_2)_nCH_2CH_2OH$, but n-distribution is different as indicated below:

| | GC Area Percent | |
|---|---|---|
| n | $M_{\bar{w}} = 445$ | $M_{\bar{w}} = 490$ |
| 4 | 1.3 | 1.0 |
| 6 | 43.8 | 30.0 |
| 8 | 27.6 | 29.7 |
| 10 | 12.3 | 18.8 |
| 12 | 4.5 | 10.4 |
| 14 | 1.0 | 2.6 |
| 16 | 0.1 | 0.7 |

EXAMPLE 1

100 grams of a fluorinated alcohol having an average molecular weight of 455 was charged to a 600 milliliter (ml) stainless steel reactor in the presence of 2.5 grams of aluminum alkoxide containing mixed alkyl groups with an average carbon number of 10.7 together with 0.3 grams gaseous hydrogen fluoride (HF) at a molar ratio of HF to Al of 3.2 to 1.0 respectively. The reactor was purged with nitrogen at a rate of 400 cubic centimeters per minute (cc/min) at 150° C. for 30 minutes. Ethylene oxide was then charged to the reactor to give a total pressure of 30 pounds per square inch gauge (psig). Ethoxylation was carried out at 150° C. and 30 psig for 115 minutes. During this period, 60 grams of ethylene oxide was consumed.

EXAMPLE 2

100 grams of the alcohol described above together with 0.2 grams of $BF_3$ etherate was introduced into a 600 ml reactor. After purging with nitrogen at 50° C. at a rate of 400 cc per minute for 30 minutes, ethylene oxide was introduced to the reactor and ethoxylation was carried out at 0 to 5 psig total pressure at a temperature of 52° to 56° C. for 75 minutes. During this period 60 grams of ethylene oxide was consumed.

By-product formation in Example 1 and Example 2 was analyzed by gas chromatographic analysis. The tests indicated that the HF/aluminum alkoxide-produced product contained twice as much ethoxylated fluorinated alcohol as compared to the ethoxylate produced by the $BF_3$/etherate. Varying pressure does not affect the amounts of dioxane and glycol produced. The results are set forth in Table 1.

TABLE 1

| Experiment | Catalyst | Dioxane/ppm | Glycol/w % |
|---|---|---|---|
| 1 | HF/Al-alkoxide | 9,000 | 4.2 |
| 2 | $BF_3$ etherate | 45,000 | 8.4 |

EXAMPLE 3

Example 1 was repeated utilizing as a catalyst 24 millimoles of hydrogen fluoride and 8 millimoles of aluminum triethyl instead of the HF/alkoxide catalyst previously used. The alcohol was the same as previously used. Ethylene oxide consumption was 60 grams in 77 minutes. The yield of alkoxylated fluorinated alcohol was the same as that observed in Example 1.

EXAMPLE 4

An attempt was made to ethoxylate the alcohol of Example 1 with 1 to 5% KOH and in a separate experiment with 5% strontium nonyl phenylate. No appreciable ethoxylation occurred at 150° C. in 80 minutes.

EXAMPLE 5

A fluorinated alcohol ethoxylate prepared as described in Example 1 and containing 3.5 moles ethylene oxide per moles of fluoroalcohol (molecular weight 490 grams per mole) was prepared by HF/triethylaluminum catalyst. Surface tension reductions obtained were compared with those obtained from a standard. The standard was obtained using a commercial fluoroalcohol ethoxylate (FC-170-C, trademark of and sold by 3M Company, Saint Paul, Minn.). Surface tensions ($\gamma$) in dynes per centimeter were determined using a spinning drop interfacial tensometer. This procedure was described at the American Chemical Society Symposium series in a paper entitled "Absorption at Interface", 1975, authored by Kayias, Schechter and Wade of the University of Texas. Using this method, surface tensions were measured at 25° C. with 0.01% fluorinated ethoxylate in water. The results are set forth in Table 2.

TABLE 2

| Surface Tension at 0.01% (dyne/cm) | |
|---|---|
| Example 5 | 17 |
| Standard Surfactant | 20 |

EXAMPLE 6

Comparisons were made between the surface tensions produced at 0.01% ethoxylate concentrations in various acidic solvents at various acid strength. The results are set forth in Table 3 below.

TABLE 3

| | Surface Tension at 0.01% (dyne/cm) | |
|---|---|---|
| Solvent | Example 5 | Standard |
| 37% HCl | 15.9 | 17.2 |
| 70% $HNO_3$ | 16.1 | 18.9 |
| 96% $H_2SO_4$ | 25.1 | 37.3 |
| 98% $H_2SO_4$ | 24 | 38 |

EXAMPLE 7

Several samples of fluoroalcohols described in Example 1 were ethoxylate. Each alcohol sample was introduced into a reaction vessel in a dry box together with a weighed amount of (C$_2$H$_5$)$_3$Al(TEAL). Required amounts of HF needed to achieve a 3HF/1 TEAL molar ratio was introduced into the gas phase and was dissolved with gentle agitation of the liquid phase. A nitrogen purge was begun and the reaction vessel brought to reaction temperature. Nitrogen purge continued for 20 minutes at reaction temperature. The temperature was maintained at 150±2° C. Ethylene oxide (EO) was introduced to a 40 pounds per square inch gauge (psig) back pressure until the desired amount of EO had been reacted. The reactor was cooled, and about 5% water by weight was added, followed by a nitrogen purge at 200 cubic centimeters/minute at 120° C. for 2 hours.

Six samples were ethoxylated to various EO levels, and surface tension determined as described in Example 5 at 25°-26° C. with 2×10$^{-2}$% ethoxylate, where the water used had a δ value of 71.5 dryness/cm.

TABLE 4

| EO/% | γ/dyne cm$^{-1}$ |
|---|---|
| 29 | 17.7 |
| 35 | 17.7 |
| 42 | 18.2 |
| 25 | 17.2 |
| 31 | 17.8 |
| 44 | 18.9 |

EXAMPLE 8

Using the procedure of Example 7, 200 grams of fluoro alcohol was ethoxylated at 35 psig in the presence of 9 cc 15% TEAL in hexane plus 0.48 g HF. Reaction Rate via time is set forth in Table 5.

TABLE 5

| Reaction Rate vs Time | | |
|---|---|---|
| Time/Min. | Tem./°C. | EO/g |
| 0 | 100 | 0.0 |
| 15 | 150 | 39.4 |
| 30 | 149 | 53.9 |
| 45 | 150 | 65.7 |
| 60 | 151 | 74.9 |
| 75 | 149 | 81.5 |
| 90 | 150 | 88.0 |
| 105 | 151 | 94.6 |
| 120 | 150 | 98.5 |
| 140 | 151 | 105.1 |

Reaction rate decreases with time, but can be easily adjusted by chaging either EO pressure, catalyst concentration, or both.

While certain embodiments and details have been shown for the purpose of illustrating this invention, it will be apparent to those skilled in this art that various changes and modifications may be made herein without departing from the spirit or scope of the invention.

We claim:

1. In a method for the alkoxylation of fluorinated alcohols by contacting said alcohols with an alkoxylating agent in the presence of a catalyst, at temperatures of from about 90° C. to about 260° C., the improvement comprising using as a catalyst at least one material having a general formula selected from the group consisting of
    (1) $(R)_{q-v}MX_v$
    (2) $HF/M(OC_nR^1_{2n+1})_q$
    (3) $BF_3/M(R)_q$ and
    (4) $SiF_4/M(R)_q$
wherein M is a metal selected from the group consisting of gallium, indium, thallium, zirconium, hafnium, aluminum and titanium, v is from 1 to q−1, n is from 1 to 22, q is equal to the valence of M, and R is, independently, hydrogen, fluorine, alkyl groups containing from 1 to 20 carbon atoms, alkoxide groups containing from 1 to 20 carbon atoms, R$^1$ is, independently, hydrogen or fluorine, and X is halogen.

2. A method as described in claim 1 when carried out at temperatures of from about 100° to about 200° C.

3. A method as described in claim 2 wherein the mole ratio of HF, BF$_3$ or SiF$_4$ to M ranges from about 0.1 to about 5.0.

4. A method as described in claim 3 wherein the catalyst is selected from the group consisting of HF/Al(OC$_n$R$^1_{2n+1}$)$_3$; HF/Ti(OC$_n$R$^1_{2n+1}$)$_4$ wherein $1 \leq n \leq 20$ and R$^1$ is hydrogen or fluorine.

5. A method as described in claim 4 wherein the catalyst is formed in-situ from the same alcohols which are alkoxylated in reaction with metal alkyls.

6. A method as described in claim 5 wherein the fluorinated alcohols are selected from the group consisting $C_mF_{2m+1}(CH_2)_aOH$ wherein m is 3 or more and a is from 1 to 12.

* * * * *